United States Patent [19]
Reimink et al.

[11] Patent Number: 5,910,170
[45] Date of Patent: Jun. 8, 1999

[54] PROSTHETIC HEART VALVE STENT UTILIZING MOUNTING CLIPS

[75] Inventors: Matthew S. Reimink, St. Paul; Richard F. Schroeder, Oakdale; M. William Mirsch, II, Roseville; Michael J. Girard, Lino Lakes, all of Minn.

[73] Assignee: St. Jude Medical, Inc., St. Paul, Minn.

[21] Appl. No.: 08/992,595

[22] Filed: Dec. 17, 1997

[51] Int. Cl.⁶ ..................................................... A61F 2/24
[52] U.S. Cl. ............................................. 623/2; 623/900
[58] Field of Search ........................................ 623/2, 900

[56] References Cited

U.S. PATENT DOCUMENTS

| | | |
|---|---|---|
| 4,441,216 | 4/1984 | Ionescu et al. . |
| 4,501,030 | 2/1985 | Lane ............................................. 623/2 |
| 4,725,274 | 2/1988 | Lane et al. . |
| 5,163,955 | 11/1992 | Love et al. . |
| 5,423,887 | 6/1995 | Love et al. . |
| 5,489,298 | 2/1996 | Love et al. . |

FOREIGN PATENT DOCUMENTS 0 179 562 B1   4/1986   European Pat. Off. ................... 623/2

OTHER PUBLICATIONS

"Edwards Prima™ Stentless Bioprosthesis Modified Model 2500", by Baxter Edwards AG, Switzerland (1996).

Primary Examiner—David H. Willse
Attorney, Agent, or Firm—Hallie A. Finucane, Esq.; Westman, Champlin & Kelly, P.A.

[57] ABSTRACT

The present invention includes a prosthetic heart valve having a stent and a piece of biocompatible material. The stent includes an inflow ring and a plurality of posts, each post extending from the ring to a post tip. The piece of material extends over the stent and substantially conforms to a profile of the stent. The piece of material includes a portion which extends adjacent a post tip. A clip is provided which has a shape generally conforming to the post tip to thereby clamp the portion of the piece of material to the post tip.

15 Claims, 6 Drawing Sheets

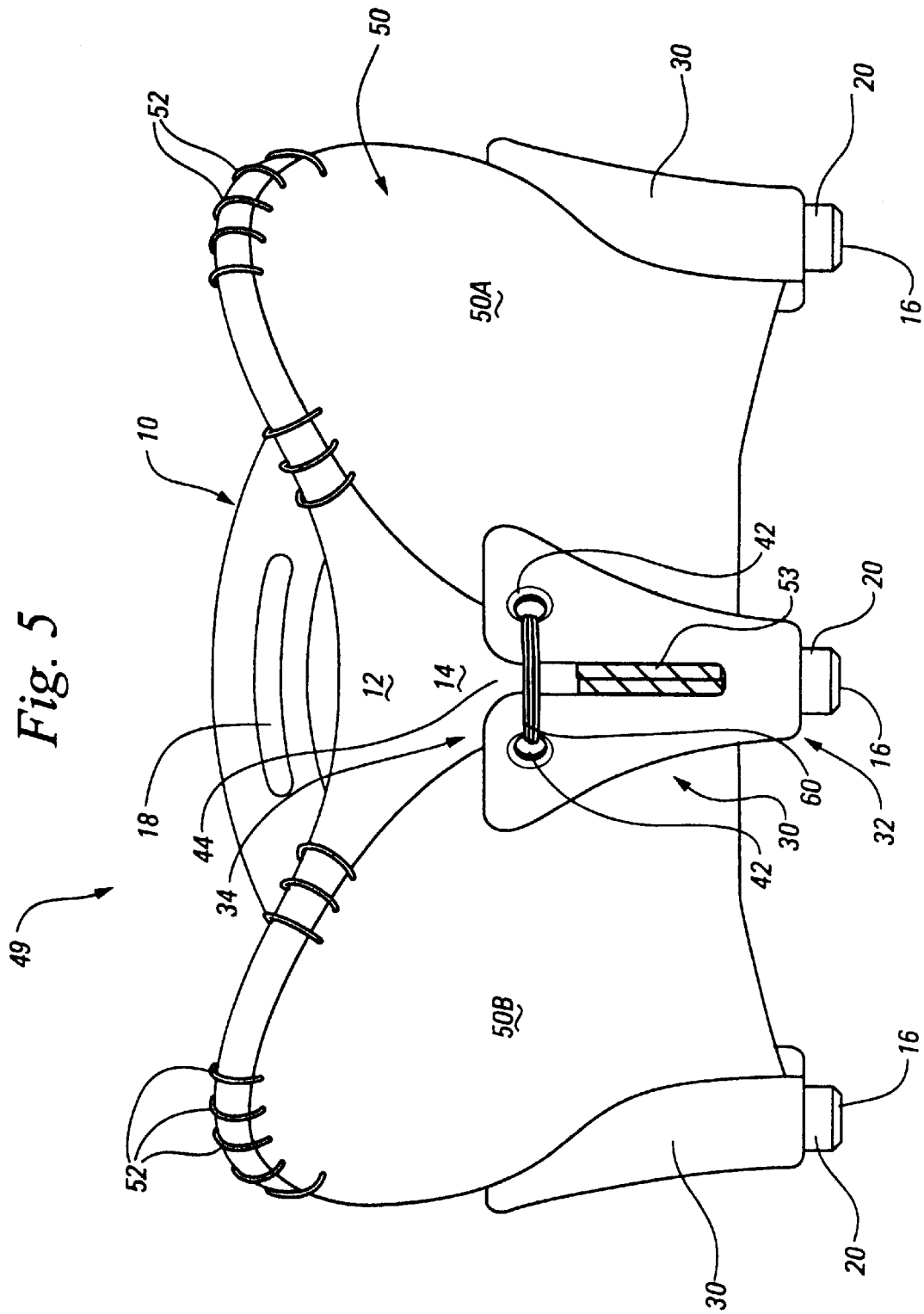

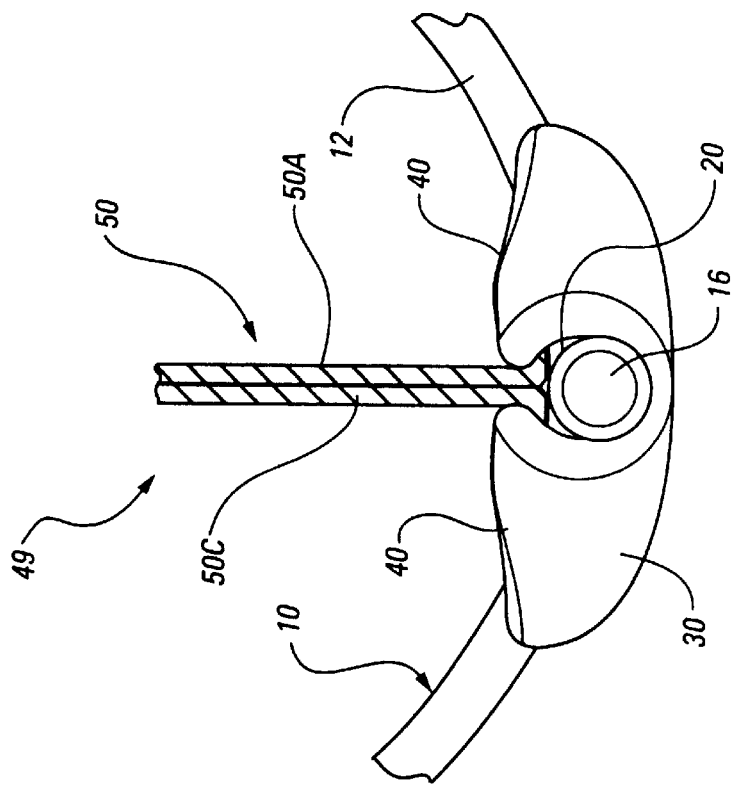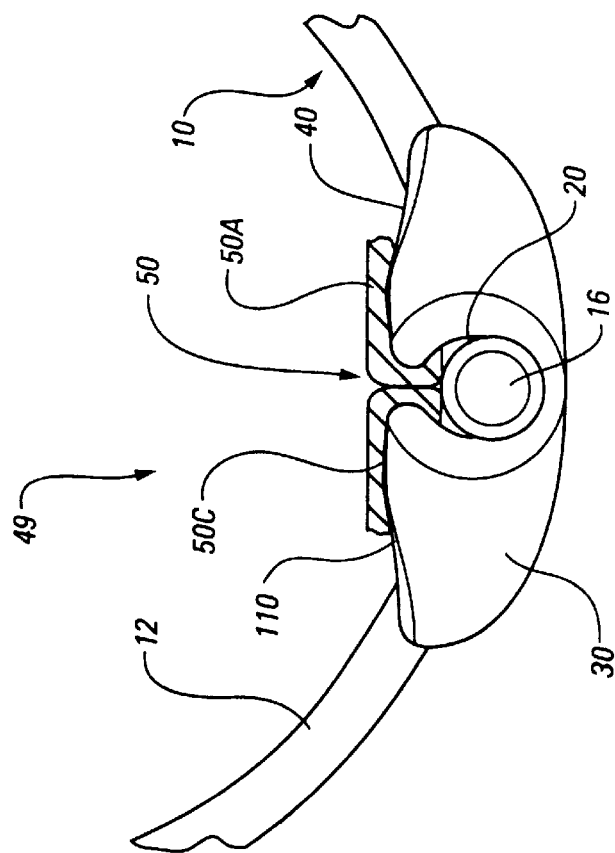

PROSTHETIC HEART VALVE STENT UTILIZING MOUNTING CLIPS

FIELD OF THE INVENTION

The present invention relates to prosthetic heart valves. More specifically, the present invention relates to attaching a biocompatible material to a stent for a prosthetic heart valve.

BACKGROUND OF THE INVENTION

Prosthetic heart valves have been used for replacing damaged heart valves in patients. Various types of prosthetic heart valves are known, including mechanical heart valves and bioprosthetic heart valves. One group of prosthetic heart valves may include a material such as tissue or synthetic polymers carried on a stent. The material typically comprises animal tissue such as porcine aortic valve material or bovine pericardium.

Various techniques are known for coupling the material to the stent. For example, suturing the valve material to the stent is one common technique used to couple the material to the stent. However, such suturing has been found to place stress on the material as the valve opens and closes, thus leading to a shorter useful life for the prosthetic heart valve. In fact, any attachment technique which creates a hole in the tissue near the post tips will concentrate destructive stresses in those areas.

Other types of attachment techniques are also shown in the prior art. For example, U.S. Pat. No. 4,501,030, issued Feb. 26, 1985, entitled "METHOD OF LEAFLET ATTACHMENT FOR PROSTHETIC HEART VALVES" describes the use of a clamping force to hold the material to the stent. However, the design uses sutures which are positioned near the top of each of the stent posts. Further, U.S. Pat. No. 4,501,030 focuses the clamping force in a small region of the material between the thin wire stent and a polymer clamping piece. By further concentrating the clamping force, the valve may be more likely to require early replacement. It may be possible to improve the performance of this device by increasing the area over which the clamping force is applied. In addition, this device applies stress to the leaflet material in direct relation to the closing load of the valve. U.S. Pat. No. 4,441,216 issued Apr. 10, 1984, entitled "TISSUE HEART VALVE AND STENT" describes the use of sutures along the top of each of the stent posts in order to attach the material to the stent. U.S. Pat. Nos. 5,163,955, 5,423,887 and 5,489,298 to Love all describe the use of alignment members at the tops of the posts. These alignment members put holes into the material. Further, the designs of Love are relatively complicated in that they require several pieces and use an inner and an outer stent which adds considerable thickness to the device. Similar problems are encountered in U.S. Pat. No. 4,725,274, to Lane which issued Feb. 16, 1988. The Lane patent requires four separate stent components which, when assembled, create a relatively thick stent.

SUMMARY OF THE INVENTION

The present invention includes a prosthetic heart valve having a stent and one or more pieces of biocompatible material which generally comprises leaflets or cusps. The stent includes an inflow ring and a plurality of posts. Each post extends from the ring to a post tip. The leaflets extend over the stent and substantially conform to a profile of the stent. The material includes a portion which extends adjacent a post tip. A clip is provided which has a shape generally conforming to the post to thereby clamp the portion of the material to the post tip. The clips reduce the stress applied to the leaflets during opening and closing of the valve. One aspect of the invention includes providing knobs at the ends of the post tips to maintain the clip in position.

BRIEF DESCRIPTION OF THE DRAWINGS

FIG. 5 is a side plan view showing commissure post clips securing material to the stent of FIG. 1.

FIG. 6A is a top plan view of a commissure post clip coupling material to a stent in which the material is in an open position.

FIG. 6B is a top plan view of a commissure post clip coupling material to a stent in which the material is in a closed position.

DETAILED DESCRIPTION OF THE PREFERRED EMBODIMENTS

Figure 1:
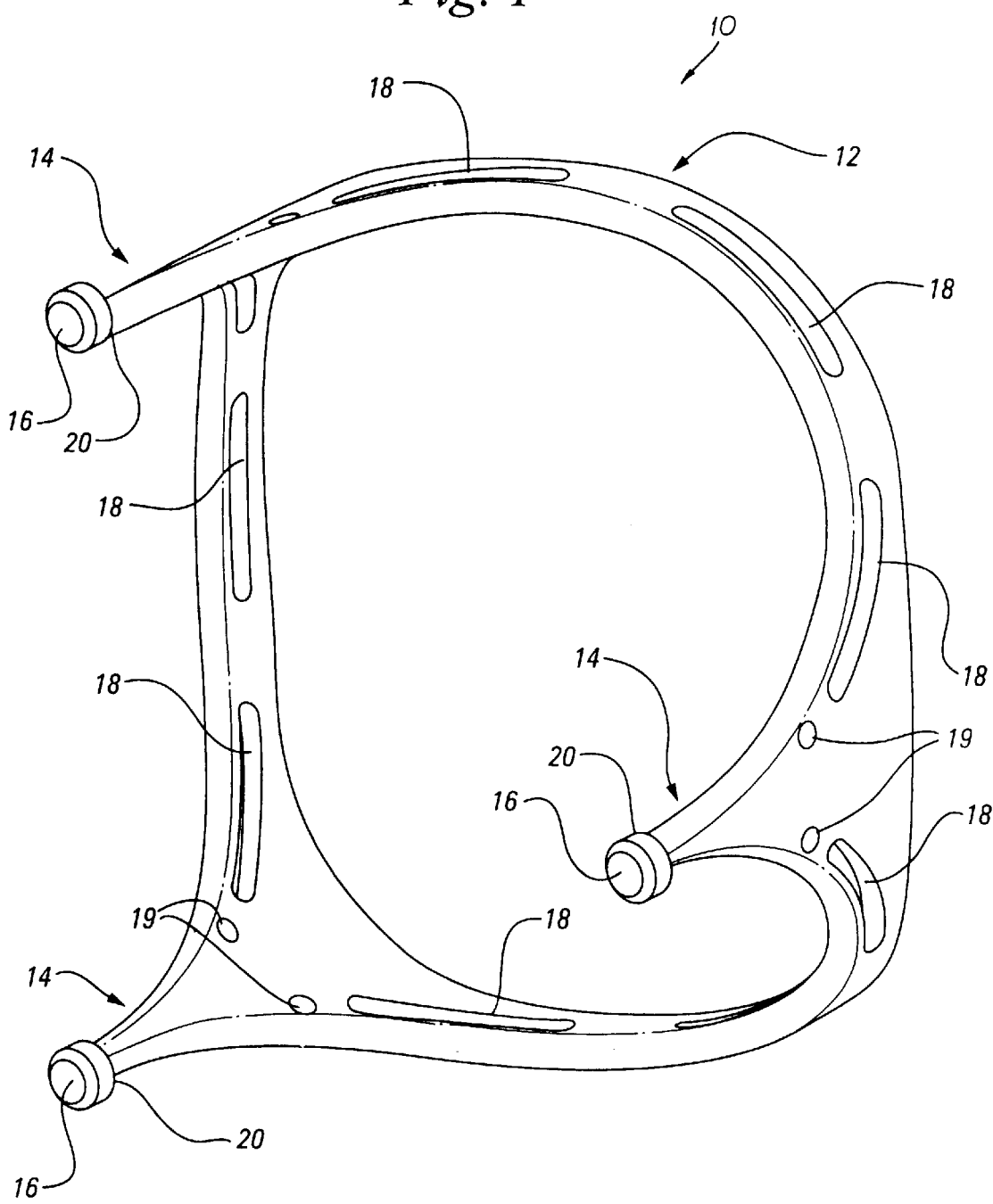
FIG. 1 is a perspective view of a stent in accordance with the present invention.

FIG. 1 is a perspective view of a stent 10 in accordance with the present invention. Stent 10 includes an inflow ring 12 which may be scalloped and commissure posts 14 extending therefrom to individual post tips 16. As shown in FIG. 1, stent 10 provides a relatively smooth profile for carrying cusps or leaflets made of biocompatible material (not shown in FIG. 1) which will hereinafter be referred to as leaflets. Stent 10 includes openings 18 and retaining holes 19 formed therein which are used to couple material (not shown in FIG. 1) to the stent. Post tip knobs 20 are carried at tips 16 of each of the commissure posts 14. Preferably, stent 10 is formed of a biocompatible material such as polyetheretherketone (PEEK).

Figure 2:
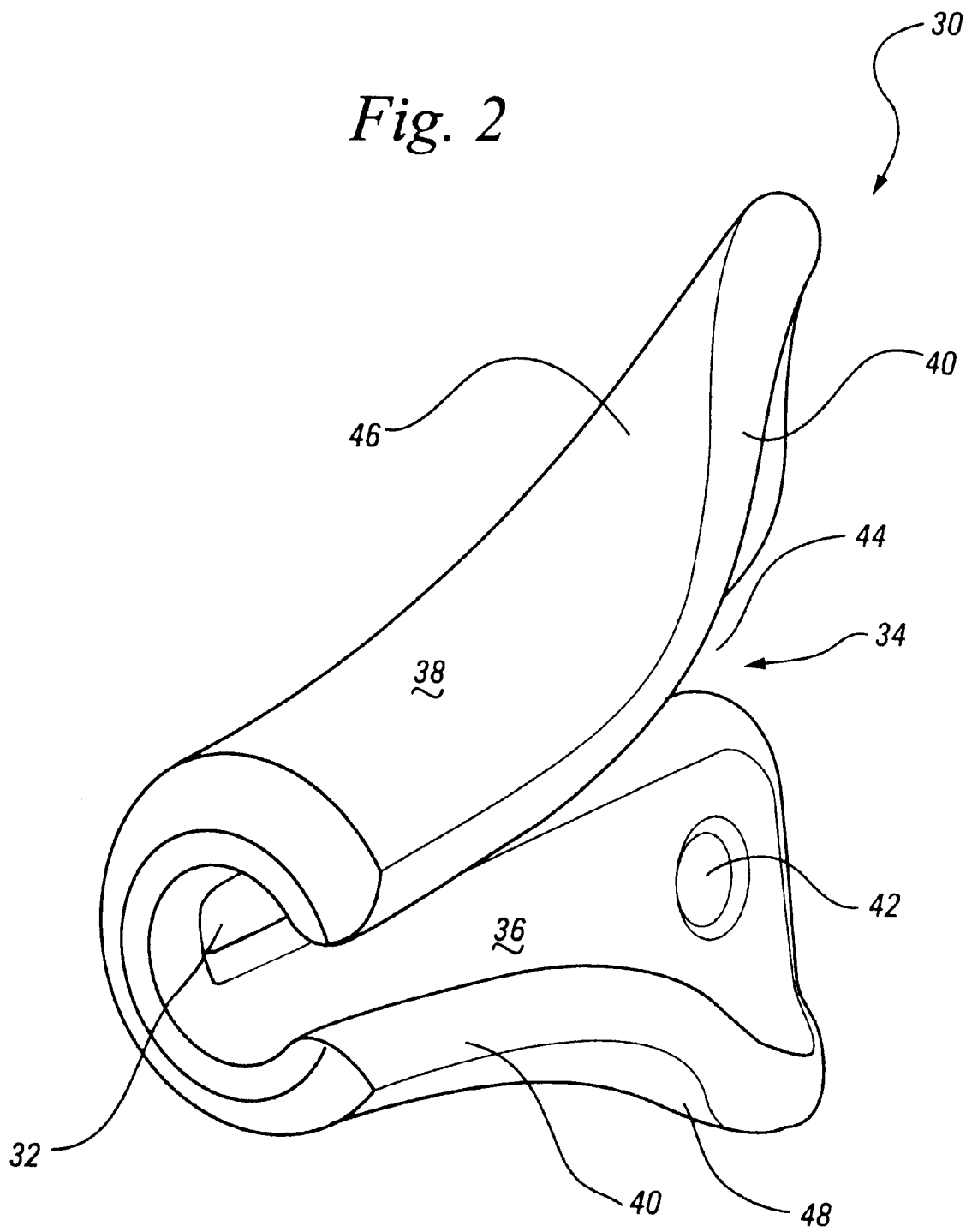
FIG. 2 is a perspective view of a commissure post clip for use with the stent of FIG. 1 in accordance with the present invention.

FIG. 2 is a perspective view of a commissure post clamp or clip 30 in accordance with one embodiment of the present invention. Commissure post clip 30 includes tip region 32, base region 34, inner side wall 36 and outer side wall 38. Inner wall 36 of clip 30 is generally formed in the shape of a C-shape and is configured to fit over posts 14 of stent 10 shown in FIG. 1 adjacent tips 16. The general C-shape of clip 30 is formed by end walls 40 which extend from tip region 32 to base region 34. Additionally, retaining holes 42 are formed in clip 30 near base region 34. Retaining holes 42 are located such that they are generally in alignment with retaining holes 19 of stent 10 when clip 30 is positioned over post 14. Clip 30 includes segmented region 44 to allow spreading between clip portions 46 and 48.

Figure 3:
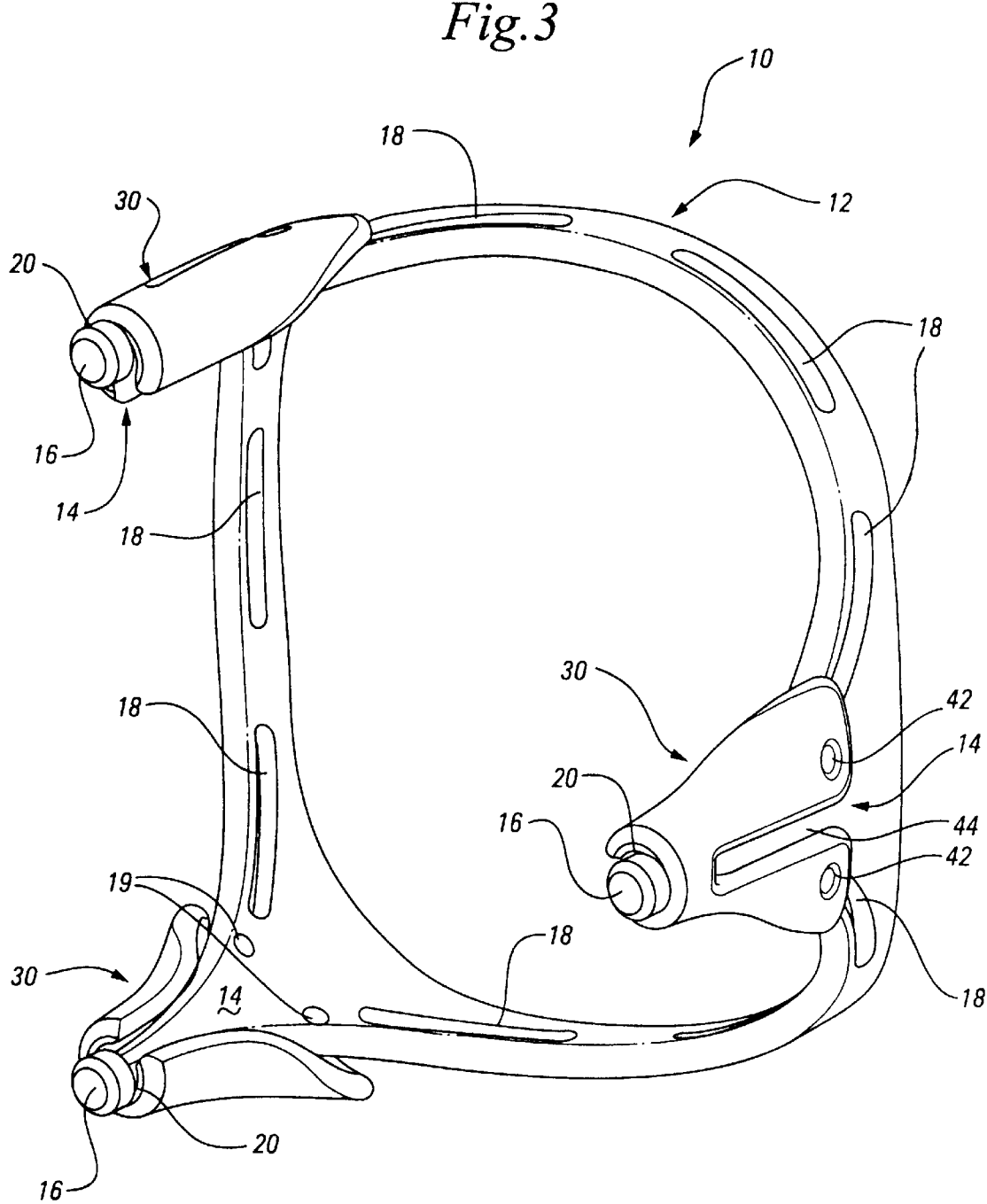
FIG. 3 is a perspective view showing three commissure post clips of the type shown in FIG. 2 coupled to posts of the stent shown in FIG. 1.

FIG. 3 is a perspective view of stent 10 including three commissure post clips 30 coupled to each post 14. For simplicity, the leaflets are not shown in FIG. 3. As shown in FIG. 3, clips 30 have a shape which is configured to generally conform to the profile of posts 14. Further, post tip knobs 20 positioned at tips 16 of posts 14 secure clips 30 on posts 14. Retaining holes 42 are substantially aligned with retaining holes 19 whereby an attachment mechanism, such as a suture (not shown in FIG. 3) can be secured proximate the base region 34 of clip 30 to couple clip 30 to a post 14. Relative pre-assembly spacing and alignment of retaining holes 19 on stent 10 and retaining holes 42 on clip 30 can be varied to adjust clamping force.

Figure 4:
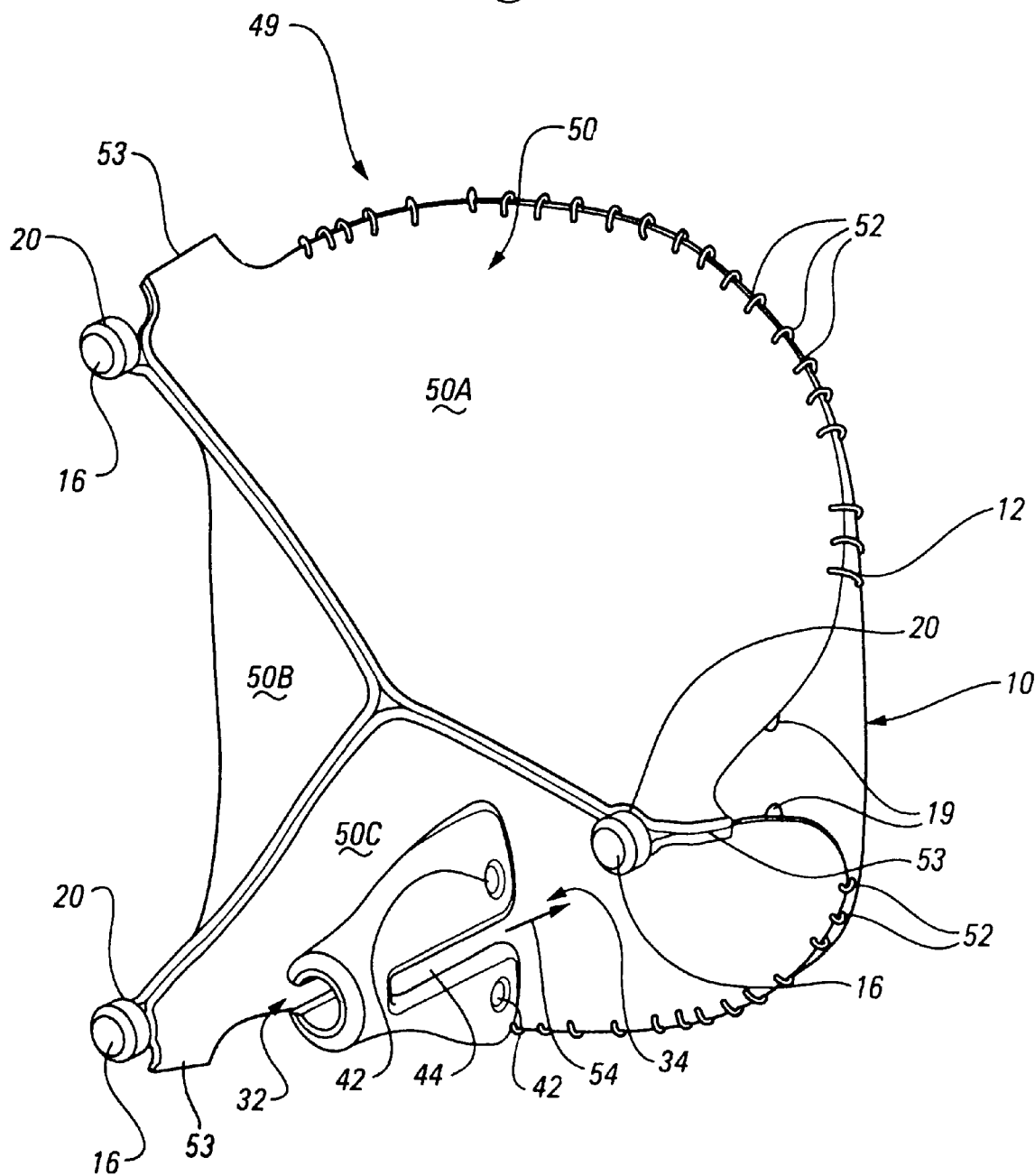
FIG. 4 is a perspective view of a prosthetic valve including a commissure post clip of FIG. 2.

FIG. 4 is an exploded view of a heart valve prosthesis 49 having stent 10 and clip 30 including leaflets 50 carried thereon. Leaflets may be a single piece or multiple pieces. In one embodiment, leaflets 50 are formed of three separate material pieces, 50A, 50B and 50C which are sewn to ring 12 using suture 52. Leaflets 50 extend over post 14 and form leaflet tabs 53 which are located generally at the tip 16 of post 14. As shown in FIG. 4, commissure post clip 30 is aligned generally coaxially with post 14 and moved in a direction shown by arrow 54. As clip 30 is moved over post 14, segmented region 44 allows clip 30 to spread such that it will securely fit over post 14 and post tip knob 20.

FIG. 5 is a side plan view of prosthetic heart valve 49 in accordance with the present invention including clips 30 coupled to posts 14 of stent 10. As shown in FIG. 5, clips 30 are secured to posts 14 using suture 60 which extends through retaining holes 42 and retaining holes 19 (not shown in FIG. 5). Leaflet tabs 53 fit in segmented region 44. As exemplified in FIG. 5, clips 30 secure leaflets 50 to posts 14 of stent 10. Further, the securing of material 50 to post 14 places only limited stress on the leaflets. Such stress is spread out over a relatively large area and requires no sutures near post tip 16.

FIGS. 6A and 6B are top plan views of prosthetic valve 49 showing material 50 in an open and closed position, respectively. As illustrated in FIG. 6A, in the open position leaflet pieces 50A and 50C form against the smooth contour side wall 40 of clip 30. This reduces the stress on material 50 during operation of prosthetic valve 49 over the lifetime of the device.

A prosthetic valve in accordance with the present invention may be made with other types of stents than that shown specifically herein. For example, the stent may be formed of various materials and have any desired flexibility for a particular application. The posts, or commissure supports may be formed as desired having other characteristics, tapering or configurations. The locations and the number of the posts may also be varied. A prosthetic heart valve in accordance with the invention may include a fabric covering or wrap, and/or a sewing ring or cuff. The construction, design and placement of these features are well known in the art. While a stent and the clip in accordance with the invention may be produced of any biocompatible material, e.g., material compatible with blood and/or tissue, practical considerations suggest the use of commercially, medically available materials. For example, these parts may be formed or preformed from any metal, synthetic polymer, biopolymer, etc. which is capable of functioning as required, or may be composite materials. It may also be desirable to sterilize the material by exposure to gas plasma, steam, gamma or electron beam irradiation, or chemical sterilization such as ethylene oxide, formaldehyde, glutaraldehyde, peroxides, and propylene oxide, and preferably any such material is capable of withstanding such exposure. The invention is not limited to the material used to construct the stent and includes other materials, their mixtures, etc.

Suitable synthetic polymers for use as a stent or clip include, but are not limited to, thermoplastics, such as polyolefins, polyesters, polyamides, polysulfones, acrylics, polyacrylonitriles, and polyaramides. Examples, include, but are not limited to polyetheretherketone (PEEK).

Suitable biopolymers for the stent or clip are biomolecules that have a repeating or polymer-like structure, including but not limited to, natural polymers such as collagen or elastin, or synthetic biopolymers, such as polyaminoacids or synthetic proteins, polysaccharides and mixtures or composites thereof.

Suitable metals for the stent or clip include, but are not limited to, cobalt, titanium, and alloys thereof. For example, an alloy sold under the trademark Eligiloy® is a cobalt-chromium-nickel-molybdenum-iron alloy (ASTM F1058).

Suitable ceramics for use as a stent or clip include, but are not limited to, alumina, zirconia, carbides, nitrides, and cermets. Closely related carbons could also be used. For example, pyrolytic carbon has desirable properties and is widely used in various heart valves.

Preferred materials are synthetic, polymeric materials, and most preferred are materials that can be injection molded. The selected material needs to have both the required stress and strain characteristics as well as good long term mechanical stability. Certain metals, such as Eligiloy®, may be advantageously used, as well as various polymers or biopolymers. PEEK is known to have mechanical properties in the desirable range, including a tensile strength of 14.5; a flexural modulus of 594.0; and a flexural strength of 24.65 (all in ksi at 73° F.). PEEK is also advantageous in that it has a high fatigue endurance limit, a low rate of creep, a low rate of water absorption at equilibrium, and significant radiation resiliency for the purposes of sterilization. At present, the most desirable starting material for use in forming a stent according to the present invention is PEEK.

The biocompatible material for the leaflets preferably includes both biological or synthetic polymers which could be either naturally occurring or artificially produced.

Biological material for use in this invention includes relatively intact tissue as well as decellularized or otherwise modified tissue. These tissues may be obtained from, for example, heart valves, pericardial tissue, dura mater, fascia, skin or any other membranous tissue. Generally, the tissue is composed of collagen-containing structures derived from different animal species such as human, bovine, porcine, equine, seal, or kangaroo, as well as engineered tissues. Engineered tissue typically involves repopulated matrices which can be derived from the tissues mentioned above or synthetically fabricated. The biological tissue may be fixed to cross-link the tissue and provide mechanical stabilization by preventing enzymatic degradation of the tissue, although the matrices do not necessarily need to be fixed. Glutaraldehyde is typically used to fix the material, but other fixation methods, such as epoxides, other difunctional aldehydes, or photooxidation can be used.

Synthetic, biocompatible materials for use in the prosthesis of the present invention include synthetic polymers as well as biological polymers. Synthetic polymers include polyamides (nylon), polyesters, polystyrene, polyacrylates, vinyl polymers (e.g. polyethylene, polytetraflouroethylene, polypropylene and polyvinylchoride), polycarbonate, polyurethane, polydimethyl siloxane, cellulose acetate, polymethyl, methacrylate, ethylene vinyl acetate, polysulfone, and similar copolymers. Biological polymers include natural forms such as collagen, elastin and cellulose or purified biopolymers such as polyaminoacids or polysaccharides. All of these materials can be used singularly or in a combination thereof and can be molded or cast into the selected forms or can be knit or woven into a mesh to form a matrix.

Materials which comprise either the stent, clips or leaflets can remain untreated or can be treated to effect a desired result, for example, to make the part(s) more effective within the environment of the heart. The modification could be in the form of surface finish alterations or in chemical modifications applied to the stent, clip or leaflet material. Surface finish alterations could include adding texture to the inside of the clip and/or the outside of the commissure post to increase the friction force imparted on the leaflet material by the clip, effectively increasing the clamping force. Surface texture could also be added to the external surfaces of the stent, clip or leaflet to optimize cell adhesion and growth. The degree of texturing must be controlled such that cell adhesion is encouraged without introducing the possibility of increased thrombolytic problems. To achieve this end, the surface finish of some portions of the stent and clip may require a reduction in roughness. Ideally, the surface finish of different surface locations on the stent and clip may be tuned independently to optimize the characteristics of the entire prosthesis. Other surface finish modifications may be implemented to increase the wetting surface tension, to decrease the harmful effects of some sterilization protocols, or to ease production.

Appropriate chemical modifications to these materials can include any or all of the following. Thrombogenicity of the surface can be modified, for example with heparin. Other modifiers such as fibronectin or other arginine-glycine-aspartic acid (RGD) sequence containing peptides can be used to modify the healing response of the part(s). Additionally, growth factors such as fibroblast or endothelial cell growth factors or other chemotactants can be applied to improve biocompatability.

Problems associated with calcification can be mitigated by the application of anticalcifics such as multivalent ions and diphosphonates. The part(s) can also be modified to reduce the potential of microbial colonization by treating them with antimicrobial compounds such as silver or gold or with any of a host of commonly available antibiotics.

The present invention is particularly advantageous because it provides a simple and secure technique for coupling a biocompatible material to a stent. Further, the clips set forth herein distribute stresses over a relatively large area of the material to thereby reduce localized stress which can lead to damage to the valve material. The present invention utilizes a permanent clamping force between the clip and the stent which is independent of the closing load of the valve. The edges of the clips are preferably rounded to provide a smooth bending radius for the leaflets when they are in the open position, thereby reducing flexural stresses. The radius of the clip can be optimized to reduce leaflet stresses and strains based on the thickness of the leaflet material. For example, calculations for bending indicate that the leaflet strain is equivalent to the leaflet thickness divided by twice the bending radius. The configuration of the stent and clip also allows the open leaflets to wrap around the outside surface of the clip, increasing the valve's orifice size. The increased orifice results in improved hemodynamics. Assembly of the device is quick and simple and the clip is self aligning with the post and material tab. The clip opens slightly to allow the material tab to fit in the segmented region of the clip. Further, the configuration of the clip and the post ensure that the clip is securely fit against and aligned with the post and the tissue tabs aid in alignment of leaflets to ensure coaptation. The clip is easily sutured to the stent.

However, other attachment techniques may be used including wire ties, staples, rivets, etc. Alternatively, the clip could be welded or glued to the commissure post following assembly. The design of the present invention minimizes the amount of hand labor required, facilitating the use of automated equipment to increase valve to valve consistency.

Although the present invention has been described with reference to preferred embodiments, workers skilled in the art will recognize that changes may be made in form and detail without departing from the spirit and scope of the invention.

What is claimed is:

1. A prosthetic heart valve, comprising:

a stent having an inflow ring and a plurality of posts, each post extending from the ring to a post tip;

biocompatible leaflet material extending over the stent and substantially conforming to a profile of the stent, the material including a plurality of portions each of which extends adjacent a post tip; and a clip having a shape generally conforming around one of the plurality of posts to clamp one of the portions of the material to the one of the plurality of posts.

2. The prosthetic heart valve of claim 1 including a post tip knob located at the post tip to maintain the clip on the one of the plurality of posts.

3. The prosthetic heart valve of claim 1 wherein the clip has an elongated generally 'C' shape.

4. The prosthetic heart valve of claim 3 wherein the clip substantially conforms to a profile of the one of the plurality of posts.

5. The prosthetic heart valve of claim 1 wherein the clip comprises a polymer.

6. The prosthetic heart valve of claim 1 wherein the stent comprises a polymer.

7. The prosthetic heart valve of claim 1 wherein the clip comprises a metal.

8. The prosthetic heart valve of claim 1 including a means for coupling the clip to the stent proximate the ring.

9. The prosthetic heart valve of claim 8 including a suture coupling the clip to the one of the plurality of posts.

10. The prosthetic heart valve of claim 9 wherein the clip includes retaining holes to receive the suture therethrough.

11. The prosthetic heart valve of claim 9 wherein the stent includes an opening for receiving the suture therethrough.

12. The prosthetic heart valve of claim 1 including a plurality of clips to clamp respective, adjacent portions of material to each of the plurality of posts.

13. The prosthetic heart valve of claim 1 wherein the clip includes a segmented region formed therein and the material includes a tab which fits in the segmented region to aid alignment and ensure leaflet coaptation.

14. The prosthetic heart valve of claim 1 wherein the material moves between an open position and a closed position and the clip includes a curved side wall, the material pressing against the curved side wall when in the open position.

15. The prosthetic heart valve of claim 1 wherein each of the plurality of posts taper in a direction toward the post tip and the clip has a shape generally conforming to the taper.

* * * * *